(12) United States Patent
Thierbach et al.

(10) Patent No.: US 11,198,895 B2
(45) Date of Patent: Dec. 14, 2021

(54) **METHOD FOR THE FERMENTATIVE PRODUCTION OF L-LYSINE USING AN L-LYSINE EXCRETING BACTERIUM OF THE SPECIES *CORYNEBACTERIUM GLUTAMICUM* HAVING A COMPLETELY OR PARTLY DELETED WHIB4 GENE**

(71) Applicant: Evonik Operations GmbH, Essen (DE)

(72) Inventors: Georg Thierbach, Bielefeld (DE); Frank Schneider, Halle (DE); Kornelia Voß, Langenselbold (DE); Thomas Bekel, Halle (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/297,019

(22) PCT Filed: Nov. 27, 2019

(86) PCT No.: PCT/EP2019/082697
§ 371 (c)(1),
(2) Date: May 26, 2021

(87) PCT Pub. No.: WO2020/109367
PCT Pub. Date: Jun. 4, 2020

(65) Prior Publication Data
US 2021/0355515 A1 Nov. 18, 2021

(30) Foreign Application Priority Data
Nov. 29, 2018 (EP) ..................................... 18209063

(51) Int. Cl.
| C12P 13/08 | (2006.01) |
| C07K 1/30 | (2006.01) |
| C12N 1/20 | (2006.01) |
| C07K 1/18 | (2006.01) |
| C12R 1/15 | (2006.01) |

(52) U.S. Cl.
CPC ................ *C12P 13/08* (2013.01); *C07K 1/18* (2013.01); *C07K 1/306* (2013.01); *C12N 1/20* (2013.01); *C12R 2001/15* (2021.05)

(58) Field of Classification Search
CPC ............................. C12P 13/08; C12R 2001/15
See application file for complete search history.

(56) References Cited

U.S. PATENT DOCUMENTS

| 5,275,940 A | 1/1994 | Kino et al. |
| 5,279,744 A | 1/1994 | Itoh et al. |
| 5,431,933 A | 7/1995 | Binder et al. |
| 5,688,671 A | 11/1997 | Sugimoto et al. |
| 5,763,230 A | 6/1998 | De Hollander et al. |
| 5,770,409 A | 6/1998 | Pfefferle et al. |
| 5,990,350 A | 11/1999 | Stevens et al. |
| 6,025,169 A | 2/2000 | Nakamura et al. |
| 6,420,151 B1 | 7/2002 | Eikmanns et al. |
| 6,844,176 B1 | 1/2005 | Bathe et al. |
| 6,893,848 B1 | 5/2005 | Yokoi et al. |
| 7,338,790 B2 | 3/2008 | Thierbach et al. |
| 7,585,650 B2 | 9/2009 | Bathe et al. |
| 7,754,446 B2 | 7/2010 | Bathe et al. |
| 9,422,568 B2 | 8/2016 | Jessberger et al. |
| 2005/0014234 A1 | 1/2005 | Zelder et al. |
| 2009/0117624 A1 | 5/2009 | Bathe et al. |
| 2015/0329883 A1 | 11/2015 | Chung et al. |

FOREIGN PATENT DOCUMENTS

| EP | 1 094 111 | 8/2006 |
| EP | 1 108 790 | 9/2009 |
| EP | 0 841 395 | 11/2011 |
| EP | 2 796 555 | 8/2018 |
| WO | 03/040181 | 5/2003 |
| WO | 2004/013341 | 2/2004 |
| WO | 2008/033001 | 3/2008 |
| WO | 2009/141330 | 11/2009 |

OTHER PUBLICATIONS

International Search Report dated Feb. 7, 2020 in PCT/EP2019/082697.
Written Opinion dated Feb. 7, 2020 in PCT/EP2019/082697.
M. J. Bush, "*The antinobacterial WhiB-like (Wbl) family of transcription factors*," Molecular Microbiology, Dec. 2018, vol. 110, No. 5, pp. 663-676.
Blombach et al., "*Acetohydroxyacid Synthase, a Novel Target for Improvement of L-Lysine Production by Corynebacterium glutamicum*", Applied and Environmental Microbiology, vol. 75, No. 2, Jan. 2009, pp. 419-427.
Choi et al., "*The whcA gene plays a negative role in oxidative stress response of Corynebacterium glutamicum*", FEMS Microbiology Letters, vol. 290, 2009, pp. 32-38.
Follettie et al., "*Gene Structure and Expression of the Corynebacterium flavum N13 ask-asd Operon*", Journal of Bacteriology, vol. 175, No. 13, Jul. 1993, pp. 4096-4103.
Kalinowski et al., "*The complete Corynebacterium glutamicum ATCC 13032 genome sequence and its impact on the production of $_L$-aspartate-derived amino acids and vitamins*", Journal of Biotechnology, vol. 104, 2003, pp. 5-25.
Lee et al., "*Regulatory interaction of the Corynebacterium glutamicum whc genes in oxidative stress responses*", Journal of Biotechnology, vol. 168, 2013, pp. 149-154.

(Continued)

*Primary Examiner* — Suzanne M Noakes

(74) *Attorney, Agent, or Firm* — Grüneberg and Myers PLLC

(57) ABSTRACT

Fermentative production of L-lysine using an L-lysine excreting bacterium of the species *Corynebacterium glutamicum* having a completely or partly deleted whiB4 gene is provided.

12 Claims, No Drawings
Specification includes a Sequence Listing.

(56) References Cited

OTHER PUBLICATIONS

Lindroth et al., "*High Performance Liquid Chromatographic Determination of Subpicomole Amounts of Amino Acids by Precolumn Fluorescence Derivatization with o-Phthaldialdehyde*", Analytical Chemistry, vol. 51, No. 11, Sep. 1979, pp. 1667-1674.
Ikeda et al., "*The Corynebacterium glutamicum genome: features and impacts on biotechnological processes*", Appl. Microbiol. Biotechnol., vol. 62, 2003, pp. 99-109.
Michael V. Pickering, "*Ion-Exchange Chromatography of Free Amino Acids*", LG-GC, vol. 7, No. 6, pp. 484-490.
Peters-Wendisch et al., "*Pyruvate carboxylase from Corynebacterium glutamicum: characterization, expression and inactivation of the pyc gene*", Microbiology, vol. 144, 1998, pp. 915-927.
Schäfer et al., "*Small mobilizable multi-purpose cloning vectors derived from the Escherichia coli plasmids pK18 and pK19: selection of defined deletions in the chromosome of Corynebacterium glutamicum*", Gene, vol. 145, 1994, pp. 69-73.
Schwarzer et al., "*Manipulation of Corynebacterium glutamicum by gene disruption and replacement*", Bio/technology, vol. 9, Jan. 1991, pp. 84-87.
Silberbach et al., "*Adaptation of Corynebacterium glutamicum to Ammonium Limitation: a Global Analysis Using Transcriptome and Proteome Techniques*", Applied and Environmental Microbiology, May 2005, vol. 71, No. 5, pp. 2391-2402.
Spackman et al., "*Automatic Recording Apparatus for use in the Chromatography of Amino Acids*", Analytical Chemistry, vol. 30, 1958, pp. 1190-1206.

METHOD FOR THE FERMENTATIVE PRODUCTION OF L-LYSINE USING AN L-LYSINE EXCRETING BACTERIUM OF THE SPECIES *CORYNEBACTERIUM GLUTAMICUM* HAVING A COMPLETELY OR PARTLY DELETED WHIB4 GENE

CROSS-REFERENCE TO RELATED APPLICATIONS

This application is the National Stage entry under § 371 of International Application No. PCT/EP2019/082697, filed on Nov. 27, 2019, and which claims the benefit of European Application No, 18209063.9, filed on Nov. 29, 2018. The content of each of these applications is hereby incorporated by reference in its entirety.

REFERENCE TO A SEQUENCE LISTING

The present application is accompanied by an ASCII text file as a computer readable form containing the sequence listing entitled, "003331USPCT_SL_ST25.txt", created on Apr. 23, 2021, with a file size of 27,871 bytes, the content of which is hereby incorporated by reference in its entirety.

BACKGROUND OF THE INVENTION

Field of the Invention

L-lysine is used in human medicine, in the pharmaceutical industry, in the food industry and particularly in nutrition of animals.

Description of Related Art

L-lysine is produced by fermentation of strains of the species *Corynebacterium glutamicum*. Because of the great economic importance, work is continually being done on improving the production methods. Improvements may relate to the fermentation technology such as e.g. stirring and supplying oxygen, or to the composition of the nutrient media e.g. the sugar concentration during fermentation, or to the processing of the fermentation broth to a suitable product form by e.g. drying and granulating the fermentation broth or ion exchange chromatography or may relate to the intrinsic performance properties of the microorganism itself.

The methods used for improving the performance properties of these microorganisms are those of mutagenesis, selection and screening of mutants. Methods of recombinant DNA technology have likewise been used for a number of years for improvement of L-lysine-producing strains of the species *Corynebacterium glutamicum*, by modifying, i.e. enhancing or attenuating, individual genes involved in L-lysine biosynthesis and investigating the effect on L-lysine production.

The nucleotide sequences of the chromosomes of various bacteria or strains resp. of the species *Corynebacterium glutamicum*, and their analysis have been disclosed. This information is available at publicly accessible databases and may be used for strain development purposes. One such database is the GenBank data base of the NCBI (National Center for Biotechnology Information, U.S. National Library of Medicine 8600 Rockville Pike, Bethesda Md., 20894 USA).

During the annotation procedure for a sequenced chromosome of an organism identified structures such as e.g. genes or coding sequences are furnished with a unique identifier called locus_tag by the supplier of the information to the data base.

The nucleotide sequence of the *Corynebacterium glutamicum* ATCC13032 chromosome and its analysis were described by Ikeda and Nakagawa (Applied Microbiology and Biotechnology 62, 99-109 (2003)) and in EP1108790. The information is available at the NCBI under accession number NC_003450. In the chromosome sequence disclosed under accession number NC_003450 locus_tag NCgl0275 identifies a nucleotide sequence coding for a regulatory protein. It is further annotated that the protein is similar to transcription factor WhiB. The amino acid sequence of the polypeptide is available under the identifier NP_599532.

In EP1108790 a coding sequence is disclosed under sequence 311. The corresponding amino acid sequence is disclosed under SEQ ID NO: 3811.

The nucleotide sequences of locus_tag NCgl0275 and sequence 311 of EP1108790 are identical.

The nucleotide sequence of the *Corynebacterium glutamicum* ATCC13032 chromosome and its analysis were independently described by Kalinowski et al. (Journal of Biotechnology 104 (1-3), 5-25 (2003)). The information is available at the NCBI under accession number NC_006958. Locus_tag CGTRNA_RS01480 identifies a nucleotide sequence coding for a gene product described as a WhiB family transcriptional regulator. The old_locus_tag designation cg0337 is also used in the art. The amino acid sequence of the polypeptide is available under the identifier WP_003863319.

The nucleotide sequences of locus_tag NCgl0275 and CGTRNA_RS01480 are identical.

Information concerning transcription signals of the gene identified by old_locus_tag cg0337 can be found in Pfeifer-Sancar et al. (BMC Genomics 14:888 (2013)).

Choi et al. (FEMS Microbiology Letters 290, 32-38 (2009) identified the NCgl0275 gene product as a WhiB like protein of *Corynebacterium glutamicum* and designated the gene as whcA. Choi et al suggested that the whcA gene plays a negative role in oxidative stress response of *Corynebacterium glutamicum*. During these studies Choi et al constructed a deletion within the whcA gene of strain AS019E12. Strain AS019E12 originates from ATCC13059 (see: Follettie et al.; Journal of Bacteriology 175(13), 4096-4103 (1993)).

Lee et al. (Journal of Biotechnology 168(2):149-54 (2013)) also refer to the whcA gene of *Corynebacterium glutamicum* as whiB4.

Silberbach et al. (Applied and Environmental Microbiology 71(5), 2391-2402 (2005)) mention the whiB4 gene having the NCBI no. NCgl0275 in a list of genes responding to long term ammonium limitation.

WO03/040181 describes genes coding for regulatory proteins, modulation of their functions and their use for the production of fine chemicals. SEQ ID NO:12 of WO03/040181 shows the amino acid sequence of a polypeptide with a functional annotation as cell division transcription factor WHMD (see identifier RXA00593). It also discloses a variant containing valine at position 18 of the amino acid sequence instead of alanine. The amino acid sequence disclosed under SEQ ID NO:12 of WO03/040181 is identical to the amino acid sequence disclosed under locus_tag NCgl0275.

US20150329883 describes a genetically engineered *Corynebacterium glutamicum* having increased activity of the NCgl0275 gene product and its use for the production of succinic acid.

WO 2004/013341 A1 describes the fermentative production of L-lysine by providing a *Corynebacterium* comprising a feedback resistant aspartate kinase and a reduced or eliminated expression of the transcription factor MikE17.

SUMMARY OF THE INVENTION

Object of the present invention is to provide new measures for the fermentative production of L-lysine by bacteria of the species *Corynebacterium glutamicum*.

To achieve the object outlined above the present invention makes available a novel method for the fermentative production of L-lysine using bacteria of the species *Corynebacterium glutamicum*, having the ability to excrete L-lysine, modified by eliminating the transcription factor WhiB4 (identified by locus_tag NCgl0275) which comprises the amino acid sequence of SEQ ID NO: 2 prior to said elimination.

The present invention further makes available methods for the manufacturing of a product containing said L-lysine from the fermentation broth.

The objects underlying the present invention were solved by the means as written in the claims.

Accordingly, the present invention provides the following:

A method for the fermentative production of L-lysine comprising the steps of
a) providing a bacterium of the species *Corynebacterium glutamicum* comprising the following features:
 having the ability to excrete L-lysine,
 containing a polynucleotide, preferably in its chromosome, encoding an aspartate kinase polypeptide insensitive to inhibition by mixtures of L-lysine and L-threonine, preferably comprising the amino acid sequence of SEQ ID NO:4, wherein the amino acid threonine at position 311 is substituted by isoleucine, and
 modified by eliminating a polypeptide comprising the amino acid sequence of SEQ ID NO:2, preferably encoded by the nucleotide sequence of SEQ ID NO:1 positions 1001 to 1348, and having the activity of a transcriptional factor, wherein said eliminating is achieved by deleting at least the part of the coding sequence corresponding to amino acids of positions 31 to 92 of said polypeptide,
b) cultivating the bacterium in a suitable medium under suitable conditions,
c) accumulating said L-lysine in the medium to form an L-lysine containing fermentation broth.

SEQ ID NO:2 relates to the amino acid sequence of the polypeptide prior to said eliminating.

The part of the coding sequence corresponding to amino acid positions 31 to 92 of SEQ ID NO:2 extends from positions 1091 to 1276 of SEQ ID NO:1.

It was found that the modified bacteria, provided in the method according to the invention, excreted L-lysine into a suitable medium under suitable fermentation conditions in an increased manner with respect to one or more parameters selected from product concentration (i.e. amount of L-lysine produced per volume, or mass unit resp., of medium/fermentation broth (e.g. g/l or g/kg)), product yield (i.e. amount of L-lysine produced per carbon source consumed (e.g. g/g or kg/kg)), product formation rate (i.e. amount of L-lysine produced per volume, or mass unit resp., of medium/fermentation broth and unit of time (e.g. g/l×h or g/kg×h)), and specific product formation rate (i.e. amount of L-lysine produced per unit of time and mass unit of the producer (e.g. g/h×g dry mass)) as compared to the unmodified bacterium.

In a preferred embodiment the bacterium provided in the method according to the invention is modified by deleting at least the part of the coding sequence corresponding to amino acid positions 10 to 113 of SEQ ID NO:2.

The part of the coding sequence corresponding to amino acid positions 10 to 113 of SEQ ID NO:2 extends from positions 1028 to 1339 of SEQ ID NO:1.

In another preferred embodiment the bacterium provided in the method according to the invention is modified by deleting at least the complete coding sequence shown in SEQ ID NO:1, positions 1001 to 1348, preferably by deleting at least the complete coding sequence and the adjoining stop codon shown in SEQ ID NO:1, positions 1001 to 1351.

The term L-lysine, where mentioned herein, in particular in the context of product formation, also comprises their ionic forms and salts, for example L-lysine mono hydrochloride or L-lysine sulfate.

For practicing the present invention bacteria of the species *Corynebacterium glutamicum* are used. Suitable bacteria for the method of this invention are L-lysine excreting strains of *Corynebacterium glutamicum*, for example L-lysine excreting strains obtained by one or several steps of strain development from strain ATCC13032 and the like and modified as described in this invention.

Strain ATCC13032 (also available as DSM20300) is the taxonomic type strain of the species *Corynebacterium glutamicum*.

A multitude of L-lysine excreting strains of the genus *Corynebacterium*, in particular of the species *Corynebacterium glutamicum* were obtained in the art during the past decades starting from strains such as ATCC13032, ATCC14067, ATCC13869 and the like. They were obtained as a result of strain development programs using inter alia methods like classical mutagenesis, selection for antimetabolite resistance as well as amplification and promotor modification of genes of the biosynthetic pathway of the L-lysine by genetic engineering methods.

DETAILED DESCRIPTION OF THE INVENTION

L-lysine excreting strains of the species *Corynebacterium glutamicum* are widely known in the art and can be modified as described in the present invention. For example, U.S. Pat. No. 7,338,790 B2 describes strain DM1797. It is also deposited at the DSMZ under accession number DSM16833. DM1797 is an aminoethylcystein resistant mutant of strain ATCC13032 obtained after N'-methyl-N-nitro-nitrosoguanidine mutagenesis. For example, Blombach et al. (Applied and Environmental Microbiology 75(2), 419-427, 2009) describe strain DM1933, which is deposited also under accession DSM25442 at the DSMZ. Strain DM1933 was obtained from ATCC13032 by several steps of strain development. Furthermore, L-lysine excreting *Corynebacterium glutamicum* strain DM2031, deposited at the DSMZ as DSM32514 may be used. Strain DM2031 is a further developed derivative of DM1933 having enhanced L-lysine excretion ability. Other L-lysine excreting *Corynebacterium glutamicum* strains are e.g. described in WO2008033001 and EP0841395.

The L-lysine excreting strains of the species *Corynebacterium glutamicum* used in the process according to the invention contain a polynucleotide, preferably in its chromosome, coding for an aspartate kinase polypeptide variant insensitive to inhibition by mixtures of L-lysine and L-threonine. Said variants are also known as feedback resistant aspartate kinase in the art.

A feedback resistant aspartate kinase polypeptide variant means an aspartate kinase which is less sensitive, or insensitive to inhibition by mixtures of L-lysine and L-threonine, e.g. 10 mM each, or mixtures of the L-lysine analogue S-(2-aminoethyl)-L-cysteine and L-threonine, e.g. 50 mM S-(2-aminoethyl)-L-cysteine and 10 mM L-threonine, when compared to the wild form of the enzyme, which is contained in wild strains like for example ATCC13032, ATCC14067 and ATCC13869. The EC number for aspartate kinase is EC 2.7.2.4. Descriptions of polynucleotides of Corynebacterium glutamicum encoding a feedback resistant aspartate kinase polypeptide variant are for example given in U.S. Pat. Nos. 5,688,671, 6,844,176 and 6,893,848. A summarizing list can be found inter alia in WO2009141330. The symbol used in the art for a gene coding for an aspartate kinase polypeptide typically is lysC. The abbreviation ask is also found. In case the gene codes for a feedback resistant polypeptide variant the art typically uses symbols like lysC$^{fbr}$ with fbr indicating feedback resistance. The art also uses the term aspartokinase for aspartate kinase.

Accordingly, said L-lysine excreting strains of the species Corynebacterium glutamicum modified as described in the present invention preferably contain at least one copy of a polynucleotide coding for an aspartate kinase polypeptide variant insensitive to inhibition by mixtures of L-lysine and L-threonine.

Said polynucleotide encoding said aspartate kinase polypeptide variant can be expressed by its natural promoter, i.e. the promoter contained in strain ATCC13032, or any other suitable promoter known in the art.

SEQ ID NO:3 shows the nucleotide sequence of the coding sequence of the aspartate kinase polypeptide of strain ATCC13032 and SEQ ID NO:4 the amino acid sequence of the encoded polypeptide. It is known in the art (cf. U.S. Pat. No. 6,893,848) that exchange of the amino acid Thr at position 311 of SEQ ID NO:4 for Ile makes the enzyme less sensitive to inhibition by mixtures of L-lysine and L-threonine.

Accordingly, it is preferred that the amino acid sequence of said aspartate kinase polypeptide variant comprises the amino acid sequence of SEQ ID NO:4 containing isoleucine at position 311.

Said amino exchange can be achieved by exchanging the nucleobase cytosine (c) at position 932 of SEQ ID NO:3 to give thymine (t). The acc codon for threonine is thus altered to the atc codon for isoleucine.

Accordingly, it is preferred that the nucleotide sequence of said aspartate kinase polypeptide variant comprises the nucleotide sequence of SEQ ID NO:3 containing thymine at position 932.

It is further known in the art that exchange of the gtg start codon of the coding sequence for the aspartate kinase polypeptide for atg enhances expression of the polypeptide (see e.g. EP2796555).

Accordingly, in a further embodiment the nucleotide sequence coding for said aspartate kinase polypeptide variant begins with an atg start codon.

A transcription factor or sequence-specific DNA-binding factor is a polypeptide that controls the rate of transcription of genetic information from DNA to messenger RNA, by binding to a specific DNA sequence.

The term DSM denotes the depository Deutsche Sammlung für Mikroorganismen and Zellkulturen (i.e. DSMZ) located in Braunschweig, Germany. The term ATCC denotes the depository American Type Culture Collection located in Manassas, Va., US.

Corynebacterium glutamicum, in particular strain ATCC13032 and L-lysine excreting strains obtained therefrom during a strain development program, contain in their chromosome a, in particular one, gene encoding a polypeptide comprising the amino acid sequence of SEQ ID NO:2. The function of the polypeptide is broadly described as a transcription factor in the art. The coding sequence is shown in SEQ ID NO:1, positions 1001 to 1348. The coding sequence may contain silent mutations which do not alter the amino acid sequence of the polypeptide. This context is also known as degeneracy of the genetic code in the art.

During the work for the present invention L-lysine excreting bacteria of the species Corynebacterium glutamicum were modified by eliminating the WhiB4 polypeptide from the bacterium. Said eliminating was achieved by deleting at least the part of the coding sequence of the polypeptide corresponding to amino acid positions 31 to 92 of SEQ ID NO:2. It was found that said modification increased their ability to excrete L-lysine in a fermentative process as compared to the unmodified bacterium.

The skilled artisan is aware of a number of methods of mutagenesis how to achieve said eliminating in the Corynebacterium glutamicum.

A common method of mutating genes of Corynebacterium glutamicum is the method of gene replacement described by Schwarzer and Pühler (Bio/Technology 9, 84-87 (1991)) and further elaborated by Schäfer et al. (Gene 145, 69-73 (1994)).

Peters-Wendisch et al. (Microbiology 144, 915-927 (1998)) used the gene replacement method to inactivate the pyc gene of Corynebacterium glutamicum encoding pyruvate carboxylase. In U.S. Pat. No. 7,585,650 the method was applied to the zwf gene to realize an amino acid exchange at position 321 of the amino acid sequence of the Zwf sub-unit of the glucose 6-phosphate dehydrogenase. Schafer et al. used the method to incorporate a deletion into the hom-thrB gene region of Corynebacterium glutamicum. In EP1094111 the method was used to incorporate a deletion into the pck gene of Corynebacterium glutamicum encoding phosphoenol pyruvate carboxykinase.

In the gene replacement method, a mutation, for example, a deletion, insertion or substitution of at least one nucleobase, is provided by an isolated polynucleotide comprising the nucleotide sequence of the gene in question or a part thereof containing the mutation.

The nucleotide sequence comprising the site of mutagenesis within the gene can be amplified by PCR using primers selected from SEQ ID NO:1 or SEQ ID NO:5 or SEQ ID NO:6. By sequencing the PCR product the desired mutants are identified. Details concerning this approach can be found inter alia in U.S. Pat. No. 7,754,446.

In the context of the present invention the nucleotide sequence of the gene in question is the whiB4 gene identified by NCgl0275.

In the context of the present invention the mutation is a deletion of at least the part of the coding sequence corresponding to amino acids of positions 31 to 92 of the encoded amino acid sequence (see SEQ ID NO:1 and SEQ ID NO:2) of the polypeptide.

As a consequence of said deletion mutation the polypeptide is eliminated from the Corynebacterium glutamicum.

As a consequence of said eliminating by deleting a novel junction point or junction site resp. of two nucleotides is created in the chromosome of the Corynebacterium glutamicum.

Said junction point may also be referred to as site of mutation.

The mutated nucleotide sequence of the gene in question or a part thereof containing the mutation comprises i) a nucleotide sequence at the 5'-end of the site of mutation, which is also referred to as 5'-flanking sequence or upstream sequence in the art, ii) a nucleotide sequence at the 3'-end of the site of mutation, which is also referred to as 3'-flanking sequence or downstream sequence in the art, and iii) the nucleotide sequence of the site of mutation between i) and ii). Due to said deletion mutation the site of mutation is, besides the lack of a specific sequence, also characterized by the flanking sequences forming the novel junction point.

Said 5'-flanking sequence and 3'-flanking sequence are required for homologous recombination and typically have a length of at least 200 bp, at least 400 bp, at least 600 bp or at least 800 bp. The maximum length typically is 1000 bp, 1500 bp or 2000 bp.

An example of a polynucleotide comprising a mutated nucleotide sequence in the context of the present invention is shown in SEQ ID NO:5. It lacks the coding sequence and the adjoining stop codon shown in SEQ ID NO:1. The nucleotide sequence of SEQ ID NO:5 from positions 17 to 816 being the 5'-flanking sequence corresponds to SEQ ID NO:1 from positions 201 to 1000. The nucleotide sequence of SEQ ID NO:5 from positions 817 to 1616 being the 3'-flanking sequence corresponds to SEQ ID NO:1 from positions 1352 to 2151.

The novel junction point created directly connects the nucleotide at position 1000 of SEQ ID NO:1 with the nucleotide at position 1352 of SEQ ID NO:1 as shown in SEQ ID NO:5 positions 816 to 817. Said novel junction point can be identified by a nucleotide sequence comprising attgtcttaatt as shown in SEQ ID NO:5 from position 811 to 822.

The polynucleotide shown in SEQ ID NO:5 contains at its 5'- and 3'-end sequences useful for cloning purposes.

Another example of a polynucleotide comprising a mutated nucleotide sequence in the context of the present invention is shown in SEQ ID NO:6. It lacks the part of the coding sequence corresponding to amino acids positions 10 to 113 of SEQ ID NO:2 or corresponding to nucleotide positions 1028 to 1339 of SEQ ID NO:1, respectively. The nucleotide sequence of SEQ ID NO:6 from positions 1 to 800 being the 5'-flanking sequence corresponds to SEQ ID NO:1 from positions 228 to 1027. The nucleotide sequence of SEQ ID NO:6 from positions 801 to 1600 being the 3'-flanking sequence corresponds to SEQ ID NO:1 from positions 1340 to 2139.

The novel junction point created directly connects the nucleotide at position 1027 of SEQ ID NO:1 with the nucleotide at position 1340 of SEQ ID NO:1 as shown in SEQ ID NO:6 positions 816 to 817. Said novel junction point can be identified by a nucleotide sequence comprising gcagcgcgccgggg as shown in SEQ ID NO:6 from position 794 to 807.

The polynucleotide shown in SEQ ID NO:6 may be equipped at its 5'- and 3'-end with sequences useful for cloning purposes.

The mutated nucleotide sequence provided is cloned into a plasmid vector, e.g. pK18mobsacB described by Schafer et al. (Gene 145, 69-73 (1994)), that is not capable of autonomous replication in *Corynebacterium glutamicum*. Said plasmid vector comprising said mutated nucleotide sequence is subsequently transferred into the desired strain of *Corynebacterium glutamicum* by transformation using electroporation or conjugation. After two events of homologous recombination comprising a recombination event within the 5'-flanking sequence provided by the plasmid vector with the homologous sequence of the *Corynebacterium glutamicum* chromosome and a recombination event within the 3'-flanking sequence provided by the plasmid vector with the homologous sequence of the *Corynebacterium glutamicum* chromosome, one effecting integration and one effecting excision of said plasmid vector, the mutation is incorporated in the *Corynebacterium glutamicum* chromosome. Thus, the nucleotide sequence of the gene in question contained in the chromosome of said desired strain is replaced by the mutated nucleotide sequence. The presence of the mutation in the desired strain is then confirmed e.g. by analysis of the nucleotide sequence as described above.

An event of homologous recombination may also be referred to as crossing over.

In a fermentative process according to the invention, a *Corynebacterium glutamicum* modified in accordance with the present invention and having the ability to excrete L-lysine is cultivated in a suitable medium under suitable conditions. Due to said ability to excrete said L-lysine the concentration of the L-lysine increases and accumulates in the medium during the fermentative process and the L-lysine is thus produced.

The fermentative process may be a discontinuous process like a batch process or a fed batch process or a continuous process. A suitable medium used for the production of L-lysine by a fermentative process contains a carbon source, a nitrogen source, a phosphorus source, inorganic ions and other organic compounds as required. Suitable carbon sources include glucose, fructose, sucrose as well as the corresponding raw materials like starch hydrolysate, molasses or high fructose corn syrup. As nitrogen source organic nitrogen-containing compounds such as peptones, meat extract, soy bean hydrolysates or urea, or inorganic compounds such as ammonium sulphate, ammonium chloride, ammonium phosphate, ammonium carbonate, ammonium nitrate, ammonium gas or aqueous ammonia can be used. As phosphorus source, phosphoric acid, potassium dihydrogen phosphate or dipotassium hydrogen phosphate or the corresponding sodium-containing salts can be used. Inorganic ions like potassium, sodium, magnesium, calcium, iron and further trace elements etc. are supplied as salts of sulfuric acid, phosphoric acid or hydrochloric acid. Other organic compounds are essential growth factors like vitamins e. g. thiamine or biotin or L-amino acids e.g. L-homoserine. The media components may be added to the culture in form of a single batch or be fed in during the cultivation in a suitable manner.

During the fermentative process, the pH of the culture can be controlled by employing basic compounds such as sodium hydroxide, potassium hydroxide, ammonia or aqueous ammonia, or acidic compounds such as phosphoric acid or sulphuric acid in a suitable manner. The pH is generally adjusted to a value of 6.0 to 8.5, preferably 6.5 to 8.0. To control foaming, it is possible to employ antifoam agents such as, for example, fatty acid polyglycol esters. To maintain the stability of plasmids, it is possible to add to the medium suitable selective substances such as, for example, antibiotics. The fermentative process is preferably carried out under aerobic conditions. In order to maintain these conditions, oxygen or oxygen-containing gas mixtures such as, for example air are introduced into the culture. The fermentative process is carried out, where appropriate, at elevated pressure, for example at an elevated pressure of 0.03 to 0.2 MPa. The temperature of the culture is normally from 25° C. to 40° C., preferably from 30° C. to 37° C. In a discontinuous process, the cultivation is continued until an amount of the L-lysine sufficient for being recovered has been formed. The cultivation is then completed. This aim is normally achieved within 10 hours to 160 hours. In continuous processes, longer cultivation times are possible.

Examples of suitable media and culture conditions can be found inter alia the patent documents U.S. Pat. Nos. 5,770, 409, 5,990,350, 5,275,940, 5,763,230 and 6,025,169.

Thus, the fermentative process results in a fermentation broth which contains the desired L-lysine.

A product containing the L-lysine is then recovered or manufactured in liquid or solid from the fermentation broth.

A "fermentation broth" means a medium in which a *Corynebacterium glutamicum* described in the invention has been cultivated for a certain time and under certain conditions.

When the fermentative process is completed, the resulting fermentation broth accordingly comprises:
a) the biomass (cell mass) of the *Corynebacterium glutamicum* of the invention, said biomass having been produced due to propagation of the cells of said *Corynebacterium glutamicum*,
b) the desired L-lysine accumulated during the fermentative process,
c) the organic by-products accumulated during the fermentative process, and
d) the components of the medium employed which have not been consumed in the fermentative process.

The organic by-products include compounds, which may be formed by the *Corynebacterium glutamicum* of the invention during the fermentative process in addition to the production of the L-lysine.

The fermentation broth is removed from the culture vessel or fermentation tank, collected where appropriate, and used for providing a product containing the L-lysine, in liquid or solid form. The expression "recovering the L-lysine-containing product" is also used for this. In the simplest case, the L-lysine-containing fermentation broth itself, which has been removed from the fermentation tank, constitutes the recovered product.

The fermentation broth can subsequently be subjected to one or more of the measures selected from the group consisting of:
a) partial (>0% to <80%) to complete (100%) or virtually complete (≥80%, ≥90%, ≥95%, ≥96%, ≥97%, ≥98%, ≥99%) removal of the water,
b) partial (>0% to <80%) to complete (100%) or virtually complete (≥80%, ≥90%, ≥95%, ≥96%, ≥97%, ≥98%, ≥99%) removal of the biomass, the latter being optionally inactivated before removal,
c) partial (>0% to <80%) to complete (100%) or virtually complete (≥80%, ≥90%, ≥95%, ≥96%, ≥97%, ≥98%, ≥99%, ≥99.3%, ≥99.7%) removal of the organic by-products formed during the fermentative process, and
d) partial (>0% to <80%) to complete (100%) or virtually complete (≥80%, ≥90%, ≥95%, ≥96%, ≥97%, ≥98%, ≥99%, ≥99.3%, ≥99.7%) removal of the residual components of the medium employed or of the residual input materials resp., which have not been consumed in the fermentative process.

An abundance of technical instructions for measures a), b), c) and d) are available in the art.

Removal of water (measure a)) can be achieved inter alia by evaporation, using e.g. a falling film evaporator, by reverse osmosis or nanofiltration. The concentrates thus obtained can be further worked up by spray drying or spray granulation. It is likewise possible to dry the fermentation broth directly using spray drying or spray granulation.

Accordingly, a method according to the invention comprises extracting or substantially eliminating water from said fermentation broth. In particular at least 40% (w/w), preferred at least 90% (w/w), more preferred at least 95% (w/w) water are extracted from the fermentation broth.

Removal of the biomass (measure b)) can be achieved inter alia by centrifugation, filtration or decantation or a combination thereof.

Removal of the organic by-products (measure c) or removal of residual components of the medium (measure d) can be achieved inter alia by chromatography, e.g. ion exchange chromatography, treatment with activated carbon or crystallization. In case the organic by-products or residual components of the medium are present in the fermentation broth as solids they can be removed by measure b).

Accordingly, the manufacturing of an L-lysine product according to the invention comprises a purification step, preferably selected from the group consisting ion exchange chromatography, treatment with activated carbon or crystallization.

A downstream processing scheme for L-lysine products can be found in the article "L-lysine Production" of R. Kelle et al. (L. Eggeling and M. Bott (Handbook of *Corynebacterium glutamicum*, CRC Press, 2005)). U.S. Pat. No. 5,279, 744 teaches the manufacturing of a purified L-lysine product by ion exchange chromatography. U.S. Pat. No. 5,431,933 teaches the manufacturing of dry L-amino acid products, e. g. an L-lysine product, containing most of the constituents of the fermentation broth.

Thus, a concentration or purification of the L-lysine is achieved and a product having the desired content of said L-lysine is provided.

Analysis of L-lysine to determine its concentration at one or more time(s) during the fermentation can take place by separating the L-lysine by means of ion exchange chromatography, preferably cation exchange chromatography, with subsequent post-column derivatization using ninhydrin, as described in Spackman et al. (Analytical Chemistry 30: 1190-1206 (1958)). It is also possible to employ ortho-phthalaldehyde rather than ninhydrin for post-column derivatization. An overview article on ion exchange chromatography can be found in Pickering (LC.GC (Magazine of Chromatographic Science 7(6):484-487 (1989)). It is likewise possible to carry out a pre-column derivatization, for example using ortho-phthalaldehyde or phenyl isothiocyanate, and to fractionate the resulting amino acid derivates by reversed-phase chromatography (RP), preferably in the form of high-performance liquid chromatography (HPLC). A method of this type is described, for example, in Lindroth et al. (Analytical Chemistry 51:1167-1174 (1979)). Detection is carried out photometrically (absorption, fluorescence). A review regarding amino acid analysis can be found inter alia in the textbook "Bioanalytik" by Lottspeich and Zorbas (Spektrum Akademischer Verlag, Heidelberg, Germany 1998).

EXPERIMENTAL SECTION

A) Materials and Methods

The molecular biology kits, primers and chemicals used and some details of the methods applied are briefly described herewith.

1. Chemicals a. Kanamycin solution from *Streptomyces kanamyceticus* was purchased from Sigma Aldrich (St. Louis, USA, Cat. no. K0254).

b. Nalidixic acid sodium salt was purchased from Sigma Aldrich (St. Louis, USA, Cat. no. N4382).

c. If not stated otherwise, all other chemicals were purchased analytically pure from Merck (Darmstadt, Germany), Sigma Aldrich (St. Louis, USA) or Carl-Roth (Karlsruhe, Germany).

2. Cultivation

If not stated otherwise, all cultivation/incubation procedures were performed as described in the following:

a. LB broth (MILLER) from Merck (Darmstadt, Germany; Cat. no. 110285) was used to cultivate *E. coli* strains in liquid medium. The liquid cultures (10 ml liquid medium per 100 ml Erlenmeyer flask with 3 baffles) were incubated in the Infors HT Multitron standard incubator shaker from Infors GmbH (Bottmingen, Switzerland) at 37° C. and 200 rpm.

b. LB agar (MILLER) from Merck (Darmstadt, Germany Cat. no. 110283) was used for cultivation of *E. coli* strains on agar plates. The agar plates were incubated at 37° C. in an INCU-Line® mini incubator from VWR (Radnor, USA).

a. Brain heart infusion broth (BHI) from Merck (Darmstadt, Germany; Cat. no. 110493) was used to cultivate *C. glutamicum* strains in liquid medium. The liquid cultures (10 ml liquid medium per 100 ml Erlenmeyer flask with 3 baffles) were incubated in the Infors HT Multitron standard incubator shaker from Infors GmbH (Bottmingen, Switzerland) at 33° C. and 200 rpm.

b. Brain heart agar (BHI-agar) from Merck (Darmstadt, Germany; Cat. no. 113825) was used for cultivation of *C. glutamicum* strains on agar plates. The agar plates were incubated at 33° C. in an incubator from Heraeus Instruments with Kelvitron® temperature controller (Hanau, Germany).

3. Determining Optical Density a. The optical density of bacterial suspensions in shake flask cultures was determined at 600 nm (OD600) using the BioPhotometer from Eppendorf AG (Hamburg, Germany).

b. The optical density of bacterial suspensions produced in the Wouter Duetz (WDS) micro fermentation system (24-Well Plates) was determined at 660 nm (OD660) with the GENios™ plate reader from Tecan Group AG (Männedorf, Switzerland).

4. Centrifugation a. Benchtop centrifuge for reaction tubes with a volume up to 2 ml Bacterial suspensions with a maximum volume of 2 ml were caused to sediment using 1 ml or 2 ml reaction tubes (e.g. Eppendorf Tubes® 3810X) using an Eppendorf 5417 R centrifuge (5 min. at 13.000 rpm).

b. Benchtop centrifuge for tubes with a volume up to 50 ml Bacterial suspensions with a maximum volume of 50 ml were caused to sediment using 15 ml or 50 ml centrifuge tubes (e.g. Falcon™ 50 ml Conical Centrifuge Tubes) using an Eppendorf 5810 R centrifuge for 10 min. at 4.000 rpm.

5. DNA Isolation a. Plasmid DNA was isolated from *E. coli* cells using the QIAprep Spin Miniprep Kit from Qiagen (Hilden, Germany, Cat. No. 27106).

b. Total DNA from *C. glutamicum* was isolated using the method of Eikmanns et al. (Microbiology 140, 1817-1828, 1994).

6. Polymerase Chain Reaction (PCR)

PCR with a proof reading (high fidelity) polymerase was used to amplify a desired segment of DNA before Gibson Assembly or Sanger sequencing.

Non-proof reading polymerase Kits were used for determining the presence or absence of a desired DNA fragment directly from *E. coli* or *C. glutamicum* colonies.

a. The Phusion® High-Fidelity DNA Polymerase Kit (Phusion Kit) from New England BioLabs Inc. (Ipswich, USA, Cat. No. M0530) was used for template-correct amplification of selected DNA regions according to the instructions of the manufacturer (see table 4).

TABLE 4

Thermocycling conditions for PCR with Phusion ® High-Fidelity DNA Polymerase Kit from NEB Inc. PCR-program

| Step | Time [min.:sec.] | T [° C.] | Description |
|---|---|---|---|
| 1 | 00:30 | 98 | Initial denaturation step |
| 2 | 00:05 | 98 | Denaturation step |
| 3 | 00:30 | 60 | Annealing step |
| 4 | 00:xx | 72 | Elongation step 1 min. per kb DNA Repeat step 2 to 4: 35 x |
| 5 | 05:00 | 72 | Final Elongation step |
| 6 | Hold | 4 | Cooling step | b. Taq PCR Core Kit (Taq Kit) from Qiagen (Hilden, Germany; Cat. No. 201203) was used to amplify a desired segment of DNA in order to confirm its presence. The kit was used according to the instructions of the manufacturer (see table 5).

TABLE 5

Thermocycling conditions for PCR with Taq PCR Core Kit (Taq Kit) from Qiagen. PCR-program

| Step | Time [min.:sec.] | T [° C.] | Description |
|---|---|---|---|
| 1 | 05:00 | 94 | Initial denaturation step |
| 2 | 00:30 | 94 | Denaturation step |
| 3 | 00:30 | 52 | Annealing step |
| 4 | 01:20 | 72 | Elongation step 1 min. per kb DNA Repeat step 2 to 4: 35 x |
| 5 | 04:00 | 72 | Final Elongation step |
| 6 | Hold | 4 | Cooling step | c. SapphireAmp® Fast PCR Master Mix (Sapphire Mix) from Takara Bio Inc (Takara Bio Europe S.A.S.; Saint-Germain-en-Laye, France; Cat. No. RR350A/B) was used as an alternative to confirm the presence of a desired segment of DNA in cells taken from *E. coli* or *C. glutamicum* colonies according to the instructions of the manufacturer (see table 6).

TABLE 6

Thermocycling conditions for PCR with SapphireAmp ® Fast PCR Master Mix (Sapphire Mix) from Takara Bio Inc. PCR-program

| Step | Time [min.:sec.] | T [° C.] | Description |
|---|---|---|---|
| 1 | 01:00 | 94 | Initial denaturation step |
| 2 | 00:05 | 98 | Denaturation step |
| 3 | 00:05 | 55 | Annealing step |
| 4 | 00:05 | 72 | Elongation step Repeat step 2 to 4: 30 x |
| 5 | 04:00 | 72 | Final Elongation step |
| 6 | Hold | 4 | Cooling step | d. Primer

The oligonucleotides used were synthesized by Eurofins Genomics GmbH (Ebersberg, Germany) using the phosphoramidite method described by McBride and Caruthers (Tetrahedron Lett. 24, 245-248, 1983).

e. Template

As PCR template either a suitably diluted solution of isolated plasmid DNA or of isolated total DNA from a *C. glutamicum* liquid culture or the total DNA contained in a colony was used (colony PCR). For said colony PCR the template was prepared by taking cell material with a toothpick from a colony on an agar plate and placing the cell material directly into the PCR reaction tube. The cell material was heated for 10 sec. with 800 W in a microwave oven type Mikrowave & Grill from SEVERIN Elektrogeräte GmbH (Sundern, Germany) and then the PCR reagents were added to the template in the PCR reaction tube.

f. PCR Cycler

PCR experiments were carried out in PCR cyclers type Mastercycler or Mastercycler nexus gradient from Eppendorf AG (Hamburg, Germany).

7. Restriction Enzyme Digestion of DNA

The FastDigest restriction endonucleases (FD) and the associated buffer from ThermoFisher Scientific (Waltham, USA, Cat. No. FD0684) were used for restriction digestion of the plasmid DNA. The reactions were carried out according to the instructions of the manufacturer's manual.

8. Determining the Size of DNA Fragments

The size of DNA fragments was determined by automatic capillary electrophoresis using the QIAxcel from Qiagen (Hilden, Germany).

9. Purification of PCR Amplificates and Restriction DNA Fragments

PCR amplificates and restriction DNA fragments were cleaned up using the QIAquick PCR Purification Kit from Qiagen (Hilden, Germany; Cat. No. 28106), according to the manufacturer's instructions.

10. Determining DNA Concentration

DNA concentration was measured using the NanoDrop Spectrophotometer ND-1000 from PEQLAB Biotechnologie GmbH, since 2015 VWR brand (Erlangen, Germany).

11. Gibson Assembly

Expression vectors and vectors allowing integration of the desired mutation into the chromosome were made using the method of Gibson et al. (Science 319, 1215-20, 2008). The Gibson Assembly Kit from New England BioLabs Inc. (Ipswich, USA; Cat. No. E2611) was used for this purpose. The reaction mix, containing the restricted vector and at least one DNA insert, was incubated at 50° C. for 60 min. 0.5 µl of the Assembly mixture was used for a transformation experiment.

12. Chemical Transformation of *E. coli* a. Chemically competent *E. coli* Stellar™ cells were purchased from Clontech Laboratories Inc. (Mountain View, USA; Cat. No. 636763) and transformed according to the manufacturers protocol (PT5055-2).

These cells were used as transformation hosts for reaction mixtures obtained by Gibson Assembly. The transformation batches were cultivated overnight for approximately 18 h at 37° C. and the transformants containing plasmids selected on LB agar supplemented with 50 mg/l kanamycin.

b. *E. coli* K-12 strain S17-1 was used as donor for conjugational transfer of plasmids based on pK18mobsacB from *E. coli* to *C. glutamicum*. Strain S17-1 is described by Simon, R. et al. (Bio/Technology 1, 784-794, 1983). It is available from the American Type Culture Collection under the access number ATCC47055.

Chemically competent *E. coli* S17-1 cells were made as follows: A preculture of 10 ml LB medium (10 ml liquid medium per 100 ml Erlenmeyer flask with 3 baffles) was inoculated with 100 µl bacterial suspension of strain S17-1 and the culture was incubated overnight for about 18 h at 37° C. and 250 rpm. The main culture (70 ml LB contained in a 250 ml Erlenmeyer flask with 3 baffles) was inoculated with 300 µl of the preculture and incubated up to an OD600 of 0.5-0.8 at 37° C. The culture was centrifuged for 6 min. at 4° C. and 4000 rpm and the supernatant was discarded. The cell pellet was resuspended in 20 ml sterile, ice-cold 50 mM $CaCl_2$) solution and incubated on ice for 30 min. After another centrifugation step, the pellet was resuspended in 5 ml ice-cold 50 mM $CaCl_2$) solution and the suspension incubated on ice for 30 min. The cell suspension was then adjusted to a final concentration of 20% glycerol (v/v) with 85% sterile ice-cold glycerol. The suspension was divided into 50 µl aliquots and stored at −80° C.

To transform S17-1 cells, the protocol according to Tang et al. (Nucleic Acids Res. 22(14), 2857-2858, 1994) with a heat shock of 45 sec. was used.

13. Conjugation of *C. glutamicum*

The pK18mobsacB plasmid system described by Schafer et al. (Gene 145, 69-73, 1994) was used to integrate desired DNA fragments into the chromosome of *C. glutamicum*. A modified conjugation method of Schafer et al. (Journal of Bacteriology 172, 1663-1666, 1990) was used to transfer the respective plasmid into the desired *C. glutamicum* recipient strain. Liquid cultures of the *C. glutamicum* strains were carried out in BHI medium at 33° C. The heat shock was carried out at 48.5° C. for 9 min. Transconjugants resulting from a first recombination event were selected by plating the conjugation batch on EM8 agar (Table 7), which was supplemented with 25 mg/l kanamycin and 50 mg/l nalidixic acid. The EM8 agar plates were incubated for 72 h at 33° C.

TABLE 7

Composition of the EM8 agar.

| Components | Concentration (g/l) |
| --- | --- |
| Glucose (sterile-filtered) | 23 |
| CSL (corn steep liquor) | 30 |
| Peptone from soymeal (Merck, Germany) | 40 |
| $(NH_4)_2SO_4$ | 8 |
| Urea | 3 |
| $KH_2PO_4$ | 4 |
| $MgSO_4 \cdot 7 H_2O$ | 0.5 |
| $FeSO_4 \cdot 7 H_2O$ | 0.01 |
| $CuSO_4 \cdot 5 H_2O$ | 0.001 |
| $ZnSO_4 \cdot 7 H_2O$ | 0.01 |
| Calcium pantothenate, D(+) | 0.01 |
| Thiamine | 0.001 |
| Inositol | 0.1 |
| Nicotinic acid | 0.001 |
| Biotin (sterile-filtered) | 0.005 |
| $CaCO_3$ (autoclaved separately) | 1.6 |
| Agar-Agar (Merck, Germany) | 14 |

Sterile toothpicks were used to transfer the transconjugants onto BHI agar, which was supplemented with 25 mg/l kanamycin and 50 mg/l nalidixic acid. The agar plates were incubated for 20 h at 33° C. The cultures of the respective transconjugants produced in this manner were then propagated further for 24 h at 33° C. in 10 ml BHI medium contained in 100 ml Erlenmeyer flasks with 3 baffles. To isolate clones having encountered a second recombination event an aliquot was taken from the liquid culture, suitably diluted and plated (typically 100 to 200 µl) on BHI agar which was supplemented with 10% saccharose. The agar plates were incubated for 48 h at 33° C. The colonies growing on the saccharose containing agar plates were then examined for the phenotype kanamycin sensitivity. To do so a toothpick was used to remove cell material from the colony and to transfer it onto BHI agar containing 25 mg/l kanamycin and onto BHI agar containing 10% saccharose. The agar plates were incubated for 60 h at 33° C. Transconjugant clones that proved to be sensitive to kanamycin and resistant to saccharose were examined for integration of the desired genetic feature into the chromosome by means of PCR.

14. Determining Nucleotide Sequences

Nucleotide sequences of DNA molecules were determined by Eurofins Genomics GmbH (Ebersberg, Germany) by cycle sequencing, using the dideoxy chain termination method of Sanger et al. (Proceedings of the National Academy of Sciences USA 74, 5463-5467, 1977), on Applied Biosystems® (Carlsbad, Calif., USA) 3730xl DNA Analyzers. Clonemanager Professional 9 software from Scientific & Educational Software (Denver, USA) was used to visualise and evaluate the sequences.

15. Glycerol Stocks of E. coli and C. glutamicum Strains

For long time storage of E. coli—and C. glutamicum strains glycerol stocks were prepared. Selected E. coli clones were cultivated in 10 ml LB medium supplemented with 2 g/l glucose. Selected C. glutamicum clones were cultivated in two fold concentrated BHI medium supplemented with 2 g/l glucose. Cultures of plasmid containing E. coli strains were supplemented with 50 mg/l kanamycin. Cultures of plasmid containing C. glutamicum strains were supplemented with 25 mg/l kanamycin. The medium was contained in 100 ml Erlenmeyer flasks with 3 baffles. It was inoculated with a loop of cells taken from a colony. The culture was then incubated for about 18 h at 37° C. and 200 rpm in the case of E. coli and 33° C. and 200 rpm in the case of C. glutamicum. After said incubation period 1.2 ml 85% (v/v) sterile glycerol were added to the culture. The obtained glycerol containing cell suspension was then aliquoted in 2 ml portions and stored at −80° C.

16. Cultivation System According to Wouter Duetz

The millilitre-scale cultivation system according to Duetz (Trends Microbiol. 2007; 15(10):469-75) was used to investigate the performance of the C. glutamicum strains constructed. For this purpose, 24-deepwell microplates (24 well WDS plates) from EnzyScreen BV (Heemstede, Netherlands; Cat. no. CR1424), filled with 2.5 mL medium were used.

Precultures of the strains were done in 10 ml two fold concentrated BHI medium. The medium was contained in a 100 ml Erlenmeyer flask with 3 baffles. It was inoculated with 100 µl of a glycerol stock culture and the culture incubated for 24 h at 33° C. and 200 rpm.

After said incubation period the optical densities OD600 of the precultures were determined. The main cultures were done by inoculating the 2.5 ml medium containing wells of the 24 Well WDS-Plate with an aliquot of the preculture to give an optical density OD600 of 0.1.

As medium for the main culture CGXII medium was used. The composition of the CGXII medium is shown in table 8.

TABLE 8

Composition of Keilhauer's CGXII medium.

| Components | Concentration (g/l) |
|---|---|
| MOPS (3-(N-Morpholino) propanesulfonic acid) | 42 |
| $(NH_4)_2SO_4$ | 20 |
| Urea | 5 |
| $KH_2PO_4$ | 1 |
| $K_2HPO_4$ | 1 |
| $MgSO_4 \cdot 7\ H_2O$ | 0.25 |
| $CaCl_2$ | 0.01 |
| $FeSO_4 \cdot 7\ H_2O$ | 0.01 |
| $MnSO_4\ H_2O$ | 0.01 |
| $ZnSO_4 \cdot 7\ H_2O$ | 0.001 |
| $CuSO_4 \cdot 5\ H_2O$ | 0.0002 |
| $NiCl_2\ 6\ H_2O$ | 0.00002 |
| Biotin (sterile-filtered) | 0.0002 |
| Protocatechuic acid (sterile-filtered) | 0.03 |
| Carbon source (sterile-filtered) | as needed |
| adjust the pH to 7 with NaOH | |

These main cultures were incubated for approximately 45 h at 33° C. and 300 rpm in an Infors HT Multitron standard incubator shaker from Infors GmbH (Bottmingen, Switzerland) until complete consumption of glucose.

The glucose concentration in the suspension was analysed with the blood glucose-meter OneTouch Vita® from LifeScan (Johnson & Johnson Medical GmbH, Neuss, Germany). After cultivation the culture suspensions were transferred to a deep well microplate. A part of the culture suspension was suitably diluted to measure the OD600. Another part of the culture was centrifuged and the concentration of L-amino acids, in particular L-lysine, and residual glucose were analysed in the supernatant.

17. Amino Acid Analyser

The concentration of L-amino acids, in particular L-lysine, in the culture supernatants was determined by ion exchange chromatography using a SYKAM S433 amino acid analyzer from SYKAM Vertriebs GmbH (Fürstenfeldbruck, Germany). As solid phase a column with spherical, polystyrene-based cation exchanger (Peek LCA N04/Na, dimension 150×4.6 mm) from SYKAM was used. Depending on the L-amino acid the separation takes place in an isocratic run using a mixture of buffers A and B for elution or by gradient elution using said buffers. As buffer A an aqueous solution containing in 20 l 263 g trisodium citrate, 120 g citric acid, 1100 ml methanol, 100 ml 37% HCl and 2 ml octanoic acid (final pH 3.5) was used. As buffer B an aqueous solution containing in 20 l 392 g trisodium citrate, 100 g boric acid and 2 ml octanoic acid (final pH 10.2) was used. The free amino acids were coloured with ninhydrin through post-column derivatization and detected photometrically at 570 nm.

B) Experimental Results

Example 1

Sequence of the NCgl0275 (whiB4) gene of C. glutamicum strain DM1933 Strain DM1933 is an L-lysine excreting C. glutamicum strain described by Blombach et al. (Applied and Environmental Microbiology 75(2), 419-427, 2009). DM1933 is also deposited at the DSMZ under accession number DSM25442.

The nucleotide sequence of the chromosome of strain DM1933 was determined by Illumina whole-genome sequencing technology (Illumina Inc., San Diego, Calif., US). See e.g. Benjak et al. (2015) Whole-Genome Sequencing for Comparative Genomics and De Novo Genome Assembly. In: Parish T., Roberts D. (eds) Mycobacteria Protocols. Methods in Molecular Biology, Vol 1285. Humana Press, NY, US) and Bennet, S. (Pharmacogenomics 5(4), 433-438, 2004).

It was found that the nucleotide sequence of the NCgI0275 (whiB4) coding sequence including the nucleotide sequence upstream and downstream thereof is identical to that of ATCC13032 as shown in SEQ ID NO:1.

DM1933 contains in its chromosome a variant of the aspartokinase gene encoding a feedback resistant aspartokinase polypeptide. Said feedback resistant aspartokinase polypeptide has the amino acid sequence of SEQ ID NO:3 of the sequence listing, wherein the amino acid L-threonine (Thr) at position 311 of the amino acid sequence is replaced by L-isoleucine (Ile). In Blombach et al. (see table 1 of Blombach et al., Applied and Environmental Microbiology 75(2), 419-427, 2009) and U.S. Pat. No. 7,338,790 the abbreviation "lysC T311I" is used to indicate said exchange.

Example 2

Construction of Plasmid pK18mobsacB_DwhiB4

Plasmid pK18mobsacB_DwhiB4 was constructed to enable incorporation of a deletion, comprising the NCgI0275 (whiB4) coding sequence and the adjoining stop codon into the chromosome of a desired C. glutamicum strain. The plasmid is based on the mobilizable vector pK18mobsacB described by Schäfer et al. (Gene 145, 69-73, 1994). For the construction of pK18mobsacB_DwhiB4 the Gibson Assembly method was used.

For this purpose, three polynucleotides or DNA molecules resp. were generated: One polynucleotide called whiB4_up comprising the upstream sequence (5'-flanking sequence) and a second polynucleotide called whiB_down comprising the downstream sequence (3'-flanking sequence) of the coding sequence of NCgI0275 (whiB4). The third polynucleotide was plasmid pK18mobsacB linearized by treatment with restriction endonuclease XbaI. The polynucleotides whiB4_up and whiB4_down were fused during the Gibson Assembly process to give the polynucleotide DwhiB4, comprising the nucleotide sequence of SEQ ID NO:5, contained in pK18mobsacB_DwhiB4.

Polynucleotides whiB4_up and whiB4_down were synthesized by PCR using total DNA isolated from a C. glutamicum ATCC13032 culture as template. For PCR the Phusion Kit was used with an elongation step (see table 4, step 4) of 15 sec. For amplification of the upstream sequence (polynucleotide whiB4_up) the primers 1f-NCgI0275 and 1r-NCgI0275 and for amplification of the downstream sequence (polynucleotide whiB4_down) the primers 2f-NCgI0275 and 2r-NCgI0275_2 were used (table 9). The primers are also shown in SEQ ID NO:8 to SEQ ID NO:11 of the sequence listing.

TABLE 9

List of primers used and size of amplificates during Phusion Kit PCR.

| synthesis of amplificate | name | sequence | size [bp] |
|---|---|---|---|
| whiB4_up | 1f-NCgI0275 | GGTACCCGGGGATCCTGTCTGCATCGTGTCATTGG | 829 |
| | 1r-NCgI0275 | CCCTTGAAATTAAGACAATCTCCTTAAAATGCGCTAC | |

TABLE 9 -continued

List of primers used and size of amplificates during Phusion Kit PCR.

| synthesis of amplificate | name | sequence | size [bp] |
|---|---|---|---|
| whiB4_down | 2f-NCgI0275 | TAAGGAGATTGTCTTAATTTCAAGGGCTGGCCATT | 828 |
| | 2r-NCgI0275_2 | GCCTGCAGGTCGACTCGGCAACTCCGCCACGCC | |

The nucleotide sequence of the amplificate whiB_up is shown in SEQ ID NO:12. The nucleotide sequence of the amplificate whiB_down is shown in SEQ ID NO:13.

Amplificate whiB4_up contains a sequence of 829 nucleotides of the upstream region of the whiB4 coding sequence of ATCC13032. At its 5'-end it is equipped with a sequence overlapping with a sequence of pK18mobsacB cut with XbaI. At its 3'-end it is equipped with a sequence overlapping with a sequence of the amplificate whiB4_down.

Amplificate whiB4_down contains a sequence of 828 nucleotides of the downstream region of the whiB4 coding sequence of ATCC13032. At its 5'-end it is equipped with a sequence overlapping with a sequence of the amplificate whiB4_up. At its 3'-end it is equipped with a sequence overlapping with a sequence of pK18mobsacB cut with XbaI. Said overlapping sequences are required for the Gibson assembly technique.

Plasmid pK18mobsacB was linearized with the restriction endonuclease XbaI. The digestion mixture was controlled by capillary electrophoresis, purified and the DNA concentration quantified. To assemble the plasmid pK18mobsacB_DwhiB4 the three polynucleotides i.e. the vector pK18mobsacB cut with XbaI, the amplificate whiB_up and the amplificate whiB_down were mixed using the Gibson Assembly Kit. The assembly mixture thus obtained was used to transform chemically competent E. coli Stellar™ cells.

Thirty kanamycin resistant transformants were analyzed by colony PCR using the Sapphire Mix and the primers 1f-NCgI0275 and 2r-NCgI0275_2 according to the protocol shown in table 5. The primers are shown in table 10 and under SEQ ID NO:8 and SEQ ID NO:11 of the sequence listing. The size of the amplificates was controlled by capillary electrophoresis.

TABLE 10

List of primers used for colony PCR and size of amplificate during Taq Kit PCR.

| indication for the presence of | name | sequence | size [bp] |
|---|---|---|---|
| DwhiB4 | 1f-NCgI0275 | GGTACCCGGGGATCCTGTCTGCATCGTGTCATTGG | 1631 |
| | 2r-NCgI0275_2 | GCCTGCAGGTCGACTCGGCAACTCCGCCACGCC | |

One of the transformants thus characterized containing a plasmid of the desired size was called Stellar/pK18mobsacB_DwhiB4 and saved as a glycerol stock.

DNA of the plasmid pK18mobsacB_DwhiB4 was isolated from said transformant and the polynucleotide DwhiB created within pK18mobsacB during the Gibson assembly was analyzed by Sanger sequencing using the primers DNCgI0275_seq_1, DNCgI0275_seq_2 and pCV22_1.p shown in table 11. Said primers are also shown under SEQ ID NO:14 to SEQ ID NO:16 of the sequence listing.

TABLE 11

List of primers used for Sanger sequencing.

| Detection of | name | sequence |
|---|---|---|
| DwhiB4 | DNCgl0275_seq_1 | GCCAGTGATGACCTCTGATG |
| | DNCgl0275_seq_2 | TTCCGAACGCCTTGCAGAGC |
| | pCV22_1.p | AGGTTTCCCGACTGGAAAGC |

The analysis of the nucleotide sequence thus obtained showed that the polynucleotide DwhiB4 contained in pK18mobsacB_DwhiB4 had the nucleotide sequence presented in SEQ ID NO:5.

Example 3

Construction of Strain DM1933_ΔwhiB

The pK18mobsacB_DwhiB plasmid was used to incorporate the deletion of the complete whiB4 coding sequence and the adjoining stop codon into the chromosome of the L-lysine producer DM1933.

Said deletion of the complete whiB4 coding sequence and the adjoining stop codon is abbreviated as ΔwhiB4, DwhiB or deltawhiB4 when appropriate.

Chemically competent cells of E. coli strain S17-1 were transformed with plasmid DNA of pK18mobsacB_DwhiB4 obtained in example 2. The modified conjugation method from Schafer et al. (Journal of Bacteriology 172, 1663-1666, 1990) as described in materials and methods was used for conjugal transfer into the strain DM1933 and for selection of transconjugant clones by virtue of their saccharose resistance and kanamycin sensitivity phenotype.

Transconjugant clones were analyzed by colony PCR using the primers NcgI0275_rev, NCgI0276_rev2 and NcgI0274_fw listed in table 12, followed by size determination of the amplificates by capillary electrophoresis. The primers are also shown in SEQ ID NO:17 to SEQ ID NO:19 of the sequence listing. For PCR the Taq Kit (see table 5) was used.

TABLE 12

List of primers used for colony PCR and size of amplificate during Taq Kit PCR.

| amplification/ detection of | name | sequence | size [bp] |
|---|---|---|---|
| ΔwhiB4 | Ncgl0275_rev | GTGGCGGCAAATTGCTGCTG | 1036 |
| | NCgl0276_rev2 | ATACCAGGCATGACCGAGAC | |
| | Ncgl0274_fw | TGCAACGAGCTTTGTCAGAG | |

One of the transconjugant clones thus characterized was called DM1933_ΔwhiB4. A glycerol stock culture of the transconjugant clone was prepared and used as starting material for further investigations.

Example 4

L-Lysine Production by Strain DM1933_ΔwhiB4

Strains DM1933 (reference) and DM1933_ΔwhiB4 were analyzed for their ability to produce L-lysine from glucose by batch cultivation using the cultivation system according to Wouter Duetz. As medium CGXII containing 20 g/l glucose as carbon source was used. The cultures were incubated for 45 h until complete consumption of glucose as confirmed by glucose analysis using blood glucose-meter and the concentrations of L-lysine and optical density OD660 were determined. The result of the experiment is presented in table 13.

TABLE 13

L-lysine production by strain DM1933_ΔlmrB.

| strain | L-lysine[1] (g/l) | OD660 |
|---|---|---|
| DM1933 | 3.8 | 8.1 |
| DM1933_ΔwhiB4 | 3.9 | 8.1 |

[1]as L-lysine x HCl

The experiment shows that L-lysine production was increased in strain DM1933ΔwhiB4 as compared to the parent strain.

SEQUENCE LISTING

```
<160> NUMBER OF SEQ ID NOS: 19

<210> SEQ ID NO 1
<211> LENGTH: 2351
<212> TYPE: DNA
<213> ORGANISM: Corynebacterium glutamicum ATCC13032
<220> FEATURE:
<221> NAME/KEY: CDS
<222> LOCATION: (1001)..(1348)
<223> OTHER INFORMATION: coding sequence of NCgl0275 (whiB4)
<220> FEATURE:
<221> NAME/KEY: misc_feature
<222> LOCATION: (1349)..(1351)
<223> OTHER INFORMATION: taa stop codon

<400> SEQUENCE: 1
agccctgcaa atccacacca tcatgctcat agaacctgcg atcctcaatc gaaacgatcg      60
catccttcat cgacgtagaa atctgatcac ccccaacctc aaaccgccgc tgcgcataaa     120
```

```
tataagcaat cggctggtca gtggaatcag taatcgtcgt gacgcccggc ccgcgaccat    180
ccgtcagatc tgaaaggttg gtctgcatcg tgtcattggt acgcgcaacc gcaacgccag    240
aaagactagc gaaaggcaca agtgcgagcg caccaaggac gccagcggcg actgtagatg    300
caacgagctt tgtcagagaa ttcgtggtgg acactccaac agcctagcga taaccccggg    360
aatcgtgaac ccaagactcc aacaatgtca gccaatcttt atttattcga ctgtgcgtta    420
ctgctgacag tcggcatgct ttgggaatcc accaggcaag ctataggga ctgtagagct     480
gacgttcgga aaacgtgcag aaaccacga actgcagtcc ggaaagcgcc ccactggccc     540
ttcgccggca gccacagagg ggttagacca tttattcgca actgtgctta cacccaagaa    600
ttctccaaca agaaaaatcc ctctatcaac attttaagtg aatgacctta agggtttgcg    660
gaatgcgatc catgttccaa ctcgcctcaa gcggtatgtg tgaagcaggt ttgaagccag    720
tgatgacctc tgatggggtt agtttgtggc aatttcgggg ctggctgaaa tgcctaattt    780
tccaaaactg aatttaatga gttgagctgt ggtaagacta gtgaactgca gatatgttgg    840
acaattgtaa agtcctctcg ttggaggctt ggcagtgtgg ccataaaagt attgcccccg    900
ttggtgtgat gcattcgaca gcaaattggc tgtgtgacta cacttgcgag tgtattaagt    960
attaggccgt gcatatgtag cgcattttaa ggagattgtc atg acg tct gtg att     1015
                                            Met Thr Ser Val Ile
                                             1               5
cca gag cag cgc aac aac ccc ttt tat agg gac agc gcc aca att gct    1063
Pro Glu Gln Arg Asn Asn Pro Phe Tyr Arg Asp Ser Ala Thr Ile Ala
            10                  15                  20
tcc tcg gac cac aca gag cgt ggt gag tgg gtc act cag gca aag tgt    1111
Ser Ser Asp His Thr Glu Arg Gly Glu Trp Val Thr Gln Ala Lys Cys
        25                  30                  35
cga aat ggc gac cca gat gca ttg ttt gtt cgt ggt gca gcg caa cgc    1159
Arg Asn Gly Asp Pro Asp Ala Leu Phe Val Arg Gly Ala Ala Gln Arg
    40                  45                  50
cga gca gca gca att tgc cgc cac tgc cct gta gcc atg cag tgc tgc    1207
Arg Ala Ala Ala Ile Cys Arg His Cys Pro Val Ala Met Gln Cys Cys
55                  60                  65
gcc gat gcc tta gat aac aag gtg gaa ttc gga gtc tgg gga ggc ctg    1255
Ala Asp Ala Leu Asp Asn Lys Val Glu Phe Gly Val Trp Gly Gly Leu
70                  75                  80                  85
acc gag cgc cag cgc cgt gca ttg ctt cga aag aag ccg cac att act    1303
Thr Glu Arg Gln Arg Arg Ala Leu Leu Arg Lys Lys Pro His Ile Thr
            90                  95                  100
aac tgg gct gaa tat ttg gct cag ggg ggc gag atc gcc ggg gtt        1348
Asn Trp Ala Glu Tyr Leu Ala Gln Gly Gly Glu Ile Ala Gly Val
        105                 110                 115
taattaattt caagggctgg ccattaacgt ggtcggcttt tttgattcag ggcgcacccc    1408
aggcgcaccc caggcgcacc ccagcgcacc acaggcgcac cccagcgcac cacaggcgca    1468
ccagcccagc acaagagcca acgcaagtgt caggcacgcc agcaaagggg ctagcaagaa    1528
gcacgccccc gaagccttag aaatgcgttc cccggtagga tgattgccat gactaaatgg    1588
gaatacgcaa ctgtgccttt gattacgcat gcaactaagc agatcctcga tacttggggt    1648
gaggacggct gggagttggt ctcggtcatg cctggtatga accctgagaa cctcgttgct    1708
tacatgaagc gtgaggtggc ttagttctta tggcttctaa ttccgaacgc cttgcagagc    1768
tgggcatttc tcttccttcc gttgcagcgc ctgttgctgc gtatgttcct gcgattcaga    1828
ccggtaacca ggtgtggact tctggtcagc tgcctttcgt tgatggtcag cttccggcca    1888
ccggcaaggt tggcgctgag gtttccgctg aggatgcgga gaagttggct cgtgcggctg    1948
```

```
cgctaaacgc tcttgctgcg attgatgcgc ttgttggcat tgataaggtc actcgcgttt    2008
tgaagattgt tggtttcgtg gcgtctgctg atgatttcag tggtcagcct gctgtcgtca    2068
acggtgcttc caatttgatg ggtgaggttt tcggcgaggc tggggcgcat gcgcgttctg    2128
ctgtgggcgt ggcggagttg ccgctcaact cgcctgtcga ggtcgaggtt atcgtcgaga    2188
tcgcgcagta gcacgctttt cgacgcaaaa tgccggttcc gcacttcgtg cgaaaccggc    2248
atttttaaat tgaccctatc gtccccttag tgttcgtaag tagaaagatc gtggtctttt    2308
gattctctgg tgattgcgat ggcgatgatg gacactaggg aca                      2351
```

<210> SEQ ID NO 2
<211> LENGTH: 116
<212> TYPE: PRT
<213> ORGANISM: Corynebacterium glutamicum ATCC13032

<400> SEQUENCE: 2

```
Met Thr Ser Val Ile Pro Glu Gln Arg Asn Asn Pro Phe Tyr Arg Asp
1               5                   10                  15

Ser Ala Thr Ile Ala Ser Ser Asp His Thr Glu Arg Gly Glu Trp Val
            20                  25                  30

Thr Gln Ala Lys Cys Arg Asn Gly Asp Pro Asp Ala Leu Phe Val Arg
        35                  40                  45

Gly Ala Ala Gln Arg Arg Ala Ala Ile Cys Arg His Cys Pro Val
    50                  55                  60

Ala Met Gln Cys Cys Ala Asp Ala Leu Asp Asn Lys Val Glu Phe Gly
65                  70                  75                  80

Val Trp Gly Gly Leu Thr Glu Arg Gln Arg Arg Ala Leu Leu Arg Lys
                85                  90                  95

Lys Pro His Ile Thr Asn Trp Ala Glu Tyr Leu Ala Gln Gly Gly Glu
            100                 105                 110

Ile Ala Gly Val
        115
```

<210> SEQ ID NO 3
<211> LENGTH: 1266
<212> TYPE: DNA
<213> ORGANISM: Corynebacterium glutamicum ATCC13032
<220> FEATURE:
<221> NAME/KEY: CDS
<222> LOCATION: (1)..(1263)
<223> OTHER INFORMATION: cds of aspartokinase gene
<220> FEATURE:
<221> NAME/KEY: misc_feature
<222> LOCATION: (1264)..(1266)
<223> OTHER INFORMATION: taa stop codon

<400> SEQUENCE: 3

```
gtg gcc ctg gtc gta cag aaa tat ggc ggt tcc tcg ctt gag agt gcg         48
Met Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct         96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat        144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt        192
Glu Leu Leu Glu Leu Ala Ala Ala Val Asn Pro Val Pro Pro Ala Arg
    50                  55                  60
```

| | | | | | | | | | | | | | | | | |
|---|---|---|---|---|---|---|---|---|---|---|---|---|---|---|---|---|
| gaa | atg | gat | atg | ctc | ctg | act | gct | ggt | gag | cgt | att | tct | aac | gct | ctc | 240 |
| Glu | Met | Asp | Met | Leu | Leu | Thr | Ala | Gly | Glu | Arg | Ile | Ser | Asn | Ala | Leu | |
| 65 | | | | 70 | | | | | 75 | | | | | | 80 | |
| gtc | gcc | atg | gct | att | gag | tcc | ctt | ggc | gca | gaa | gcc | caa | tct | ttc | acg | 288 |
| Val | Ala | Met | Ala | Ile | Glu | Ser | Leu | Gly | Ala | Glu | Ala | Gln | Ser | Phe | Thr | |
| | | | | 85 | | | | | 90 | | | | | 95 | | |
| ggc | tct | cag | gct | ggt | gtg | ctc | acc | acc | gag | cgc | cac | gga | aac | gca | cgc | 336 |
| Gly | Ser | Gln | Ala | Gly | Val | Leu | Thr | Thr | Glu | Arg | His | Gly | Asn | Ala | Arg | |
| | | | 100 | | | | | 105 | | | | | 110 | | | |
| att | gtt | gat | gtc | act | cca | ggt | cgt | gtg | cgt | gaa | gca | ctc | gat | gag | ggc | 384 |
| Ile | Val | Asp | Val | Thr | Pro | Gly | Arg | Val | Arg | Glu | Ala | Leu | Asp | Glu | Gly | |
| | | | 115 | | | | | 120 | | | | | 125 | | | |
| aag | atc | tgc | att | gtt | gct | ggt | ttc | cag | ggt | gtt | aat | aaa | gaa | acc | cgc | 432 |
| Lys | Ile | Cys | Ile | Val | Ala | Gly | Phe | Gln | Gly | Val | Asn | Lys | Glu | Thr | Arg | |
| | | 130 | | | | | 135 | | | | | 140 | | | | |
| gat | gtc | acc | acg | ttg | ggt | cgt | ggt | ggt | tct | gac | acc | act | gca | gtt | gcg | 480 |
| Asp | Val | Thr | Thr | Leu | Gly | Arg | Gly | Gly | Ser | Asp | Thr | Thr | Ala | Val | Ala | |
| 145 | | | | 150 | | | | | 155 | | | | | | 160 | |
| ttg | gca | gct | gct | ttg | aac | gct | gat | gtg | tgt | gag | att | tac | tcg | gac | gtt | 528 |
| Leu | Ala | Ala | Ala | Leu | Asn | Ala | Asp | Val | Cys | Glu | Ile | Tyr | Ser | Asp | Val | |
| | | | | 165 | | | | | 170 | | | | | 175 | | |
| gac | ggt | gtg | tat | acc | gct | gac | ccg | cgc | atc | gtt | cct | aat | gca | cag | aag | 576 |
| Asp | Gly | Val | Tyr | Thr | Ala | Asp | Pro | Arg | Ile | Val | Pro | Asn | Ala | Gln | Lys | |
| | | | 180 | | | | | 185 | | | | | 190 | | | |
| ctg | gaa | aag | ctc | agc | ttc | gaa | gaa | atg | ctg | gaa | ctt | gct | gct | gtt | ggc | 624 |
| Leu | Glu | Lys | Leu | Ser | Phe | Glu | Glu | Met | Leu | Glu | Leu | Ala | Ala | Val | Gly | |
| | | 195 | | | | | 200 | | | | | 205 | | | | |
| tcc | aag | att | ttg | gtg | ctg | cgc | agt | gtt | gaa | tac | gct | cgt | gca | ttc | aat | 672 |
| Ser | Lys | Ile | Leu | Val | Leu | Arg | Ser | Val | Glu | Tyr | Ala | Arg | Ala | Phe | Asn | |
| | 210 | | | | | 215 | | | | | 220 | | | | | |
| gtg | cca | ctt | cgc | gta | cgc | tcg | tct | tat | agt | aat | gat | ccc | ggc | act | ttg | 720 |
| Val | Pro | Leu | Arg | Val | Arg | Ser | Ser | Tyr | Ser | Asn | Asp | Pro | Gly | Thr | Leu | |
| 225 | | | | 230 | | | | | 235 | | | | | 240 | | |
| att | gcc | ggc | tct | atg | gag | gat | att | cct | gtg | gaa | gaa | gca | gtc | ctt | acc | 768 |
| Ile | Ala | Gly | Ser | Met | Glu | Asp | Ile | Pro | Val | Glu | Glu | Ala | Val | Leu | Thr | |
| | | | | 245 | | | | | 250 | | | | | 255 | | |
| ggt | gtc | gca | acc | gac | aag | tcc | gaa | gcc | aaa | gta | acc | gtt | ctg | ggt | att | 816 |
| Gly | Val | Ala | Thr | Asp | Lys | Ser | Glu | Ala | Lys | Val | Thr | Val | Leu | Gly | Ile | |
| | | | 260 | | | | | 265 | | | | | 270 | | | |
| tcc | gat | aag | cca | ggc | gag | gct | gcg | aag | gtt | ttc | cgt | gcg | ttg | gct | gat | 864 |
| Ser | Asp | Lys | Pro | Gly | Glu | Ala | Ala | Lys | Val | Phe | Arg | Ala | Leu | Ala | Asp | |
| | | 275 | | | | | 280 | | | | | 285 | | | | |
| gca | gaa | atc | aac | att | gac | atg | gtt | ctg | cag | aac | gtc | tct | tct | gta | gaa | 912 |
| Ala | Glu | Ile | Asn | Ile | Asp | Met | Val | Leu | Gln | Asn | Val | Ser | Ser | Val | Glu | |
| | 290 | | | | | 295 | | | | | 300 | | | | | |
| gac | ggc | acc | acc | gac | atc | acc | ttc | acc | tgc | cct | cgt | tcc | gac | ggc | cgc | 960 |
| Asp | Gly | Thr | Thr | Asp | Ile | Thr | Phe | Thr | Cys | Pro | Arg | Ser | Asp | Gly | Arg | |
| 305 | | | | 310 | | | | | 315 | | | | | 320 | | |
| cgc | gcg | atg | gag | atc | ttg | aag | aag | ctt | cag | gtt | cag | ggc | aac | tgg | acc | 1008 |
| Arg | Ala | Met | Glu | Ile | Leu | Lys | Lys | Leu | Gln | Val | Gln | Gly | Asn | Trp | Thr | |
| | | | | 325 | | | | | 330 | | | | | 335 | | |
| aat | gtg | ctt | tac | gac | gac | cag | gtc | ggc | aaa | gtc | tcc | ctc | gtg | ggt | gct | 1056 |
| Asn | Val | Leu | Tyr | Asp | Asp | Gln | Val | Gly | Lys | Val | Ser | Leu | Val | Gly | Ala | |
| | | | 340 | | | | | 345 | | | | | 350 | | | |
| ggc | atg | aag | tct | cac | cca | ggt | gtt | acc | gca | gag | ttc | atg | gaa | gct | ctg | 1104 |
| Gly | Met | Lys | Ser | His | Pro | Gly | Val | Thr | Ala | Glu | Phe | Met | Glu | Ala | Leu | |
| | | 355 | | | | | 360 | | | | | 365 | | | | |
| cgc | gat | gtc | aac | gtg | aac | atc | gaa | ttg | att | tcc | acc | tct | gag | att | cgt | 1152 |
| Arg | Asp | Val | Asn | Val | Asn | Ile | Glu | Leu | Ile | Ser | Thr | Ser | Glu | Ile | Arg | |
| | 370 | | | | | 375 | | | | | 380 | | | | | |

```
att tcc gtg ctg atc cgt gaa gat gat ctg gat gct gct gca cgt gca    1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat    1248
Leu His Glu Gln Phe Gln Leu Gly Gly Glu Asp Glu Ala Val Val Tyr
                405                 410                 415 gca ggc acc gga cgc taa                                            1266
Ala Gly Thr Gly Arg
        420
```

<210> SEQ ID NO 4
<211> LENGTH: 421
<212> TYPE: PRT
<213> ORGANISM: Corynebacterium glutamicum ATCC13032

<400> SEQUENCE: 4

```
Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
```

```
                305                 310                 315                 320
Arg Ala Met Glu Ile Leu Lys Lys Leu Gln Val Gln Gly Asn Trp Thr
                    325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 5
<211> LENGTH: 1631
<212> TYPE: DNA
<213> ORGANISM: Artificial Sequence
<220> FEATURE:
<223> OTHER INFORMATION: nucleotide sequence comprising a deletion of
      the cds of the whiB4 gene of Corynebacterium glutamicum ATCC13032
      and the adjoining stop codon
<220> FEATURE:
<221> NAME/KEY: misc_feature
<222> LOCATION: (1)..(16)
<223> OTHER INFORMATION: sequence required for Gibson assembly
<220> FEATURE:
<221> NAME/KEY: misc_feature
<222> LOCATION: (17)..(816)
<223> OTHER INFORMATION: sequence upstream of the site of deletion
      (5'-flanking sequence)
<220> FEATURE:
<221> NAME/KEY: misc_feature
<222> LOCATION: (811)..(822)
<223> OTHER INFORMATION: sequence attgtcttaatt
<220> FEATURE:
<221> NAME/KEY: misc_feature
<222> LOCATION: (816)..(817)
<223> OTHER INFORMATION: positions identifying the site of deletion of
      the coding sequence and the adjoining stop codon of the whiB4 gene
<220> FEATURE:
<221> NAME/KEY: misc_feature
<222> LOCATION: (817)..(1616)
<223> OTHER INFORMATION: sequence downstream of the site of deletion
      (3'-flanking sequence)
<220> FEATURE:
<221> NAME/KEY: misc_feature
<222> LOCATION: (1617)..(1631)
<223> OTHER INFORMATION: sequence required for Gibson assembly

<400> SEQUENCE: 5
ggtacccggg gatcctgtct gcatcgtgtc attggtacgc gcaaccgcaa cgccagaaag      60
actagcgaaa ggcacaagtg cgagcgcacc aaggacgcca gcggcgactg tagatgcaac    120
gagctttgtc agagaattcg tggtggacac tccaacagcc tagcgataac cccgggaatc    180
gtgaacccaa gactccaaca atgtcagcca atctttattt attcgactgt gcgttactgc    240
tgacagtcgg catgctttgg gaatccacca ggcaagctat aggggactgt agagctgacg    300
ttcggaaaac gtgcagaaaa ccacgaactg cagtccggaa agcgccccac tggcccttcg    360
ccggcagcca cagaggggtt agaccattta ttcgcaactg tgcttacacc caagaattct    420
ccaacaagaa aaatccctct atcaacattt taagtgaatg accttaaggg tttgcggaat    480
gcgatccatg ttccaactcg cctcaagcgg tatgtgtgaa gcaggtttga agccagtgat    540
```

```
gacctctgat ggggttagtt tgtggcaatt tcggggctgg ctgaaatgcc taattttcca      600
aaactgaatt taatgagttg agctgtggta agactagtga actgcagata tgttggacaa      660
ttgtaaagtc ctctcgttgg aggcttggca gtgtggccat aaaagtattg ccccgttgg       720 tgtgatgcat tcgacagcaa attggctgtg tgactacact tgcgagtgta ttaagtatta     780
ggccgtgcat atgtagcgca ttttaaggag attgtcttaa tttcaagggc tggccattaa      840
cgtggtcggc ttttttgatt cagggcgcac cccaggcgca ccccaggcgc accccagcgc      900
accacaggcg caccccagcg caccacaggc gcaccagccc agcacaagag ccaacgcaag      960
tgtcaggcac gccagcaaag gggctagcaa gaagcacgcc cccgaagcct tagaaatgcg     1020
ttccccggta ggatgattgc catgactaaa tgggaatacg caactgtgcc tttgattacg     1080
catgcaacta agcagatcct cgatacttgg ggtgaggacg gctgggagtt ggtctcggtc     1140
atgcctggta tgaaccctga gaacctcgtt gcttacatga agcgtgaggt ggcttagttc     1200
ttatggcttc taattccgaa cgccttgcag agctgggcat ttctcttcct tccgttgcag     1260
cgcctgttgc tgcgtatgtt cctgcgattc agaccggtaa ccaggtgtgg acttctggtc     1320
agctgccttt cgttgatggt cagcttccgg ccaccggcaa ggttggcgct gaggtttccg     1380
ctgaggatgc ggagaagttg gctcgtgcgg ctgcgctaaa cgctcttgct gcgattgatg     1440
cgcttgttgg cattgataag gtcactcgcg ttttgaagat tgttggtttc gtggcgtctg     1500
ctgatgattt cagtggtcag cctgctgtcg tcaacggtgc ttccaatttg atgggtgagg     1560
ttttcggcga ggctggggcg catgcgcgtt ctgctgtggg cgtggcggag ttgccgagtc     1620
gacctgcagg c                                                          1631

<210> SEQ ID NO 6
<211> LENGTH: 1600
<212> TYPE: DNA
<213> ORGANISM: Artificial Sequence
<220> FEATURE:
<223> OTHER INFORMATION: nucleotide sequence comprising a deletion of
      part of the cds of the whiB4 gene of Corynebacterium glutamicum
      ATCC13032
<220> FEATURE:
<221> NAME/KEY: misc_feature
<222> LOCATION: (1)..(800)
<223> OTHER INFORMATION: sequence upstream of the site of deletion
      (5'-flanking sequence)
<220> FEATURE:
<221> NAME/KEY: CDS
<222> LOCATION: (774)..(800)
<223> OTHER INFORMATION: residual 5'-coding sequence
<220> FEATURE:
<221> NAME/KEY: misc_feature
<222> LOCATION: (794)..(807)
<223> OTHER INFORMATION: sequence gcagcgcgccgggg
<220> FEATURE:
<221> NAME/KEY: misc_feature
<222> LOCATION: (800)..(801)
<223> OTHER INFORMATION: positions identfying the site of deletion
      within the coding sequence of the whiB4 gene
<220> FEATURE:
<221> NAME/KEY: CDS
<222> LOCATION: (801)..(809)
<223> OTHER INFORMATION: residual 3'-coding sequence
<220> FEATURE:
<221> NAME/KEY: misc_feature
<222> LOCATION: (801)..(1600)
<223> OTHER INFORMATION: sequence downstream of the site of mutation
      (3'-flanking sequence)
<220> FEATURE:
<221> NAME/KEY: misc_feature
<222> LOCATION: (810)..(812)
<223> OTHER INFORMATION: taa stop codon
```

<400> SEQUENCE: 6

```
accgcaacgc cagaaagact agcgaaaggc acaagtgcga gcgcaccaag gacgccagcg      60
gcgactgtag atgcaacgag ctttgtcaga gaattcgtgg tggacactcc aacagcctag     120
cgataacccc gggaatcgtg aacccaagac tccaacaatg tcagccaatc tttatttatt     180
cgactgtgcg ttactgctga cagtcggcat gctttgggaa tccaccaggc aagctatagg     240
ggactgtaga gctgacgttc ggaaaacgtg cagaaaacca cgaactgcag tccggaaagc     300
gccccactgg cccttcgccg gcagccacag aggggttaga ccatttattc gcaactgtgc     360
ttacacccaa gaattctcca acaagaaaaa tccctctatc aacattttaa gtgaatgacc     420
ttaagggttt gcggaatgcg atccatgttc caactcgcct caagcggtat gtgtgaagca     480
ggtttgaagc cagtgatgac ctctgatggg gttagtttgt ggcaatttcg gggctggctg     540
aaatgcctaa ttttccaaaa ctgaatttaa tgagttgagc tgtggtaaga ctagtgaact     600
gcagatatgt tggacaattg taaagtcctc tcgttggagg cttggcagtg tggccataaa     660
agtattgccc ccgttggtgt gatgcattcg acagcaaatt ggctgtgtga ctacacttgc     720
gagtgtatta agtattaggc cgtgcatatg tagcgcattt taaggagatt gtc atg      776
                                                           Met
                                                           1
acg tct gtg att cca gag cag cgc gcc ggg gtt taattaattt caagggctgg      829
Thr Ser Val Ile Pro Glu Gln Arg Ala Gly Val
        5                   10
ccattaacgt ggtcggcttt tttgattcag ggcgcacccc aggcgcaccc aggcgcacc      889
ccagcgcacc acaggcgcac cccagcgcac cacaggcgca ccagcccagc acaagagcca      949
acgcaagtgt caggcacgcc agcaaagggg ctagcaagaa gcacgccccc gaagccttag     1009
aaatgcgttc cccggtagga tgattgccat gactaaatgg gaatacgcaa ctgtgccttt     1069
gattacgcat gcaactaagc agatcctcga tacttggggt gaggacggct gggagttggt     1129
ctcggtcatg cctggtatga accctgagaa cctcgttgct tacatgaagc gtgaggtggc     1189
ttagttctta tggcttctaa ttccgaacgc cttgcagagc tggcattttc tcttccttcc     1249
gttgcagcgc ctgttgctgc gtatgttcct gcgattcaga ccggtaacca ggtgtggact     1309
tctggtcagc tgccttttcgt tgatggtcag cttccggcca ccggcaaggt tggcgctgag     1369
gtttccgctg aggatgcgga gaagttggct cgtgcggctg cgctaaacgc tcttgctgcg     1429
attgatgcgc ttgttggcat tgataaggtc actcgcgttt tgaagattgt tggtttcgtg     1489
gcgtctgctg atgatttcag tggtcagcct gctgtcgtca acggtgcttc caatttgatg     1549
ggtgaggttt tcggcgaggc tggggcgcat gcgcgttctg ctgtgggcgt g            1600
```

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Met Thr Ser Val Ile Pro Glu Gln Arg
1               5

<210> SEQ ID NO 8
<211> LENGTH: 35
<212> TYPE: DNA
<213> ORGANISM: Artificial Sequence

```
<220> FEATURE:
<223> OTHER INFORMATION: primer
<220> FEATURE:
<221> NAME/KEY: misc_feature
<222> LOCATION: (1)..(35)
<223> OTHER INFORMATION: primer 1f-NCgl0275

<400> SEQUENCE: 8
ggtacccggg gatcctgtct gcatcgtgtc attgg                                35

<210> SEQ ID NO 9
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(37)
<223> OTHER INFORMATION: primer 1r-NCgl0275

<400> SEQUENCE: 9
cccttgaaat taagacaatc tccttaaaat gcgctac                              37

<210> SEQ ID NO 10
<211> LENGTH: 35
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(35)
<223> OTHER INFORMATION: primer 2f-NCgl0275

<400> SEQUENCE: 10
taaggagatt gtcttaattt caagggctgg ccatt                                35

<210> SEQ ID NO 11
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(33)
<223> OTHER INFORMATION: primer 2f-NCgl0275_2

<400> SEQUENCE: 11
gcctgcaggt cgactcggca actccgccac gcc                                  33

<210> SEQ ID NO 12
<211> LENGTH: 829
<212> TYPE: DNA
<213> ORGANISM: Artificial Sequence
<220> FEATURE:
<223> OTHER INFORMATION: amplificate whiB4_up

<400> SEQUENCE: 12
ggtacccggg gatcctgtct gcatcgtgtc attggtacgc gcaaccgcaa cgccagaaag      60
actagcgaaa ggcacaagtg cgagcgcacc aaggacgcca cgcgcgactg tagatgcaac     120
gagctttgtc agagaattcg tggtggacac tccaacagcc tagcgataac cccgggaatc     180
gtgaacccaa gactccaaca atgtcagcca atctttattt attcgactgt gcgttactgc     240
tgacagtcgg catgctttgg gaatccacca ggcaagctat aggggactgt agagctgacg     300
```

```
ttcggaaaac gtgcagaaaa ccacgaactg cagtccggaa agcgccccac tggcccttcg    360
ccggcagcca cagaggggtt agaccattta ttcgcaactg tgcttacacc caagaattct    420
ccaacaagaa aaatccctct atcaacattt taagtgaatg accttaaggg tttgcggaat    480
gcgatccatg ttccaactcg cctcaagcgg tatgtgtgaa gcaggtttga agccagtgat    540
gacctctgat ggggttagtt tgtggcaatt tcggggctgg ctgaaatgcc taattttcca    600
aaactgaatt taatgagttg agctgtggta agactagtga actgcagata tgttggacaa    660
ttgtaaagtc ctctcgttgg aggcttggca gtgtggccat aaaagtattg ccccgttgg     720 tgtgatgcat tcgacagcaa attggctgtg tgactacact tgcgagtgta ttaagtatta    780
ggccgtgcat atgtagcgca ttttaaggag attgtcttaa tttcaaggg               829
```

<210> SEQ ID NO 13
<211> LENGTH: 828
<212> TYPE: DNA
<213> ORGANISM: Artificial Sequence
<220> FEATURE:
<223> OTHER INFORMATION: amplificate whiB4_down

<400> SEQUENCE: 13

```
taaggagatt gtcttaattt caagggctgg ccattaacgt ggtcggcttt tttgattcag     60
ggcgcacccc aggcgcaccc caggcgcacc ccagcgcacc acaggcgcac cccagcgcac    120
cacaggcgca ccagcccagc acaagagcca acgcaagtgt caggcacgcc agcaaagggg    180
ctagcaagaa gcacgccccc gaagccttag aaatgcgttc cccggtagga tgattgccat    240
gactaaatgg gaatacgcaa ctgtgccttt gattacgcat gcaactaagc agatcctcga    300
tacttggggt gaggacggct gggagttggt ctcggtcatg cctggtatga accctgagaa    360
cctcgttgct tacatgaagc gtgaggtggc ttagttctta tggcttctaa ttccgaacgc    420
cttgcagagc tgggcatttc tcttccttcc gttgcagcgc tgttgctgc gtatgttcct     480 gcgattcaga ccggtaacca ggtgtggact tctggtcagc tgcctttcgt tgatggtcag    540
cttccggcca ccggcaaggt tggcgctgag gtttccgctg aggatgcgga gaagttggct    600
cgtgcggctg cgctaaacgc tcttgctgcg attgatgcgc ttgttggcat tgataaggtc    660
actcgcgttt tgaagattgt tggtttcgtg gcgtctgctg atgatttcag tggtcagcct    720
gctgtcgtca acggtgcttc caatttgatg ggtgaggttt tcggcgaggc tggggcgcat    780
gcgcgttctg ctgtgggcgt ggcggagttg ccgagtcgac ctgcaggc                 828
```

<210> SEQ ID NO 14
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer DNCgl0275_seq_1

<400> SEQUENCE: 14

```
gccagtgatg acctctgatg                                                 20
```

<210> SEQ ID NO 15
<211> LENGTH: 20
<212> TYPE: DNA
<213> ORGANISM: Artificial Sequence
<220> FEATURE:
<223> OTHER INFORMATION: primer

```
<220> FEATURE:
<221> NAME/KEY: misc_feature
<222> LOCATION: (1)..(20)
<223> OTHER INFORMATION: primer DNCgl0275_seq_2

<400> SEQUENCE: 15
ttccgaacgc cttgcagagc                                               20

<210> SEQ ID NO 16
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer pCV22_1.p

<400> SEQUENCE: 16
aggtttcccg actggaaagc                                               20

<210> SEQ ID NO 17
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Ncgl0275_rev

<400> SEQUENCE: 17
gtggcggcaa attgctgctg                                               20

<210> SEQ ID NO 18
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer NCgl0276_rev2

<400> SEQUENCE: 18
ataccaggca tgaccgagac                                               20

<210> SEQ ID NO 19
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Ncgl0274_fw

<400> SEQUENCE: 19
tgcaacgagc tttgtcagag                                               20
```

The invention claimed is:

1. A method for the fermentative production of L-lysine, comprising:
   a) providing a bacterium of the species *Corynebacterium glutamicum*, wherein the bacterium
      is capable of excreting L-lysine,
      contains a polynucleotide encoding an aspartate kinase polypeptide insensitive to inhibition by mixtures of L-lysine and L-threonine, and
      is modified by eliminating a polypeptide comprising the amino acid sequence of SEQ ID NO:2 and having the activity of a transcriptional factor, wherein said eliminating is achieved by deleting at least the coding sequence corresponding to amino acids of positions 31 to 92 of said polypeptide,
   b) cultivating the bacterium in a suitable medium under suitable conditions,
   c) accumulating said L-lysine in the medium to form an L-lysine containing fermentation broth.

2. The method of claim 1, wherein said aspartate kinase polypeptide comprises the amino acid sequence of SEQ ID NO: 4, wherein the amino acid threonine at position 311 is substituted by isoleucine.

3. The method of claim 1, wherein said eliminated polypeptide is encoded by positions 1001 to 1348 of the nucleotide sequence of SEQ ID NO:1.

4. The method of claim 1, wherein said eliminating is achieved by deleting at least the coding sequence corresponding to amino acids of positions 10 to 113 of SEQ ID NO:2.

5. The method of claim 1, wherein at least the complete coding sequence is deleted.

6. The method of claim 5, wherein at least the complete coding sequence and an adjoining stop codon is deleted.

7. The method of claim 1, wherein the fermentative production of L-lysine is performed using a process selected from the group consisting of batch process, fed batch process, and continuous process.

8. The method of claim 1, further comprising manufacturing an L-lysine containing product from said L-lysine containing fermentation broth.

9. The method of claim 1, further comprising extracting or substantially eliminating water from said L-lysine containing fermentation broth.

10. The method of claim 9, wherein at least 40% (w/w) water is extracted from the L-lysine containing fermentation broth.

11. The method of claim 8, wherein said manufacturing comprises purifying L-lysine.

12. The method of claim 11, wherein said purifying uses a technique selected from the group consisting of treatment with activated carbon, ion exchange chromatography, and crystallization.

* * * * *